US012018243B2

(12) United States Patent
Sforza (10) Patent No.: US 12,018,243 B2
(45) Date of Patent: Jun. 25, 2024

(54) FAT FRAGMENTATION DEVICE AND METHOD

(71) Applicant: The Duke Limited, Rio de Janeiro (BR)

(72) Inventor: Marcos Sforza, Rio de Janeiro (BR)

(73) Assignee: The Duke Limited, Copacabana (BR)

( * ) Notice: Subject to any disclaimer, the term of this patent is extended or adjusted under 35 U.S.C. 154(b) by 300 days.

(21) Appl. No.: 17/088,322

(22) Filed: Nov. 3, 2020

(65) Prior Publication Data

US 2022/0135930 A1 May 5, 2022

(51) Int. Cl.
*C12M 1/00* (2006.01)
*A61K 35/35* (2015.01)
*C12M 1/12* (2006.01)
*C12M 1/33* (2006.01)
*C12N 5/077* (2010.01)
*C12N 5/0775* (2010.01)

(52) U.S. Cl.
CPC ............ *C12M 47/04* (2013.01); *A61K 35/35* (2013.01); *C12M 25/02* (2013.01); *C12M 45/02* (2013.01); *C12N 5/0653* (2013.01); *C12N 5/0667* (2013.01); *C12N 2527/00* (2013.01)

(58) Field of Classification Search
CPC ...... C12M 47/04; C12M 25/02; C12M 45/02; C12N 5/0653; C12N 5/0667; C12N 2527/00; A61K 35/35
See application file for complete search history.

(56) References Cited

U.S. PATENT DOCUMENTS

| | | | |
|---|---|---|---|
| 2010/0112695 A1 | 5/2010 | Min | |
| 2013/0344589 A1 | 12/2013 | Winkler et al. | |
| 2015/0374888 A1 | 12/2015 | Shippert | |
| 2019/0232017 A1 | 8/2019 | Tremolada | |
| 2020/0061258 A1 | 2/2020 | Khalaj | |
| 2020/0131478 A1 | 4/2020 | Wang et al. | |

FOREIGN PATENT DOCUMENTS

| | | | |
|---|---|---|---|
| CN | 114729296 | 7/2022 | |
| KR | 1020230103754 | 7/2023 | |
| WO | WO-2014112794 A1 * | 7/2014 | ............ C12M 45/02 |
| WO | WO-2018235102 A1 * | 12/2018 | .......... A61M 1/0056 |
| WO | 2019012231 | 1/2019 | |
| WO | 2019145276 | 8/2019 | |
| WO | 2020008805 | 1/2020 | |
| WO | 2022096917 | 5/2022 | |

OTHER PUBLICATIONS

Machine Translation of WO2014112794A1, Jul. 24, 2014, p. 1-19. (Year: 2014).*
Sforza, Marcos; International Search Report and Written Opinion for Application No. PCTIB/2020/060324, filed Nov. 3, 2020, mailed Mar. 24, 2021, 11 pages.
Sforza, Marcos; Extended European Search Report for Serial No. 20938505.3, filed Nov. 3, 2020, mailed Jun. 19, 2023, 26 pgs.

* cited by examiner

*Primary Examiner* — Robert J Eom
(74) *Attorney, Agent, or Firm* — Taylor English Duma LLP (57) ABSTRACT

The present invention provides a device for adipose tissue processing, microfragmentation and facilitation of mechanical separation of adipose derived stem cells ("ADSCs"), methods of using the device to generate a stromal vascular fraction ("SVF") and methods of the SVF.

16 Claims, 9 Drawing Sheets

| | | | QTY. |
|---|---|---|---|
| 1 | Filter B | POLYCARBONATE | 1 |
| 2 | Filter A | POLYCARBONATE | 1 |
| 3 | Filter C | POLYCARBONATE | 1 |
| 4 | Spiral2 | POLYCARBONATE | 1 |
| 5 | Housing Side A | POLYCARBONATE | 1 |
| 6 | Housing Side B | POLYCARBONATE | 1 |

| | |
|---|---|
| MIDDLE FILTER | |
| TOP FILTER | |
| BOTTOM FILTER | |
| MIXING SPIRAL | |
| TOP OF ENCLOSURE | |
| BOTTOM OF ENCLOSURE | |

Filter 2

FAT FRAGMENTATION DEVICE AND METHOD

FIELD OF THE INVENTION

The present invention relates to a fat harvesting and processing device and method. In particular, the present invention relates to a device and method for adipose tissue harvesting, microfragmentation, facilitation of stem cell extraction and stem cell mechanical separation and nanofragmentation.

BACKGROUND OF THE INVENTION

Adipose tissue is a source of stem cells for various tissue engineering and cell therapies. In particular, the stromal vascular fraction ("SVF") derived from adipose tissue is harvested and processed, and in medical and cosmetic procedures, such SVF is used alone or with another material to generate a graft material for application to a subject. SVF contains adipose-derived stem cells (ADSCs).

A key measurement of the quality and ultimately the success of use of SVF in the biomedical and cosmetic procedures or applications is the viability of stem cells in the SVF. Viability of the stem cells largely depends from the degree of injury or impact from the various procedures in adipose tissue harvest and processing, which leads to the production of SVF.

Various techniques are developed, with limited success, aiming to minimize injury to ADSCs and exposure of ADSCs to various risk factors including environmental stress such as mechanical impact, temperature and pressure shocks, and chemical and biochemical exposures (exposure to viral or bacterial pathogens), which often lead to injury or death of ADSCs, which in turn, would illicit various adverse biochemical reactions (e.g., secretion of adverse cytokines or adverse immune reactions), leading to ultimate failure of such biomedical and cosmetic applications or procedures.

Therefore, there is a continuing need to develop new devices and methods for adipose tissue harvesting and processing for SVF.

The embodiments below address the above-identified issues and needs.

SUMMARY OF THE INVENTION

In one aspect of the present invention, it is provided a device for adipose tissue processing, microfragmentation and facilitation of mechanical separation of adipose derived stem cells ("ADSCs"), comprising:
an upper housing with an inlet,
a lower housing with an outlet,
a filter stack, and
a spiral flow effectuate,
wherein the upper housing and the lower housing are configured to join to form an enclosure that encloses the filter stack and the spiral flow effectuater,
wherein the spiral effectuate is configured to receive a flower of filtrate from the filter stack and generate a spiral flow of the adipose tissue to minimize a direct shock of the adipose tissue with walls of the filter stacker to promote enhanced mechanical separation with less trauma to cells of the adipose tissue.

In some embodiments of the invention device, optionally in combination with any or all the various embodiments disclosed herein, the filter stack comprises at least one filter having multiple holes of a size that is the same or different, the size ranging from about 0.4 mm to about 3 mm.

In some embodiments of the invention device, optionally in combination with any or all the various embodiments disclosed herein, the filter stack comprises at least one filter having multiple holes of alternating sizes.

In some embodiments of the invention device, optionally in combination with any or all the various embodiments disclosed herein, the filter stack comprises a first filter, a second filter, and a third filter, where—
the first filter having multiple holes of a size that is the same ranging from about 2.2 mm to about 1.45 mm;
the second filter having multiple holes of alternating sizes where one size that is the same ranging from about 1.8 mm to 0.9 mm and another size that is the same ranging from about 1.35 mm to about 0.6 mm; and
the third filter having multi holes of a size that is the same ranging from about 1.35 mm to about 0.45 mm.

In some embodiments of the invention device, optionally in combination with any or all the various embodiments disclosed herein, the upper housing and lower housing are joined by a tongue and groove joint joined by ultrasonic welding.

In some embodiments of the invention device, optionally in combination with any or all the various embodiments disclosed herein, the filter stack comprises more than one filters, and the more than one filters are connected via rods or tubes.

In some embodiments of the invention device, optionally in combination with any or all the various embodiments disclosed herein, the inlet and outlet comprise a Luer lock thread.

In some embodiments of the invention device, optionally in combination with any or all the various embodiments disclosed herein, the at least one of the upper housing, lower housing, the filter stack or the spiral flow effectuater is made from polycarbonate or stainless steel.

In some embodiments of the invention device, optionally in combination with any or all the various embodiments disclosed herein, the device is a disposable device.

In another aspect of the present invention, it is provided a method of producing stromal vascular fraction of adipose tissue, comprising
subjecting a volume of adipose tissue to fragmentation and separation by a device to generate a volume of fragmented adipose tissue; and
subject the fragmented adipose tissue to centrifuging to generate a volume of the stromal vascular fraction,
wherein the device is a device for adipose tissue processing, microfragmentation and facilitation of mechanical separation of adipose derived stem cells ("ADSCs"), the device comprising: an upper housing with an inlet, a lower housing with an outlet, a filter stack, and a spiral flow effectuate, where—
the upper housing and the lower housing are configured to join to form an enclosure that encloses the filter stack and the spiral flow effectuater; and
the spiral effectuate is configured to receive a flower of filtrate from the filter stack and generate a spiral flow of the adipose tissue to minimize a direct shock of the adipose tissue with walls of the filter stacker to promote enhanced mechanical separation with less trauma to cells of the adipose tissue.

In some embodiments of the invention method, optionally in combination with any or all the various embodiments disclosed herein, the filter stack comprises at least one filter having multiple holes of a size that is the same or different, the size ranging from about 0.4 mm to about 3 mm.

In some embodiments of the invention method, optionally in combination with any or all the various embodiments disclosed herein, the filter stack comprises at least one filter having multiple holes of alternating sizes.

In some embodiments of the invention method, optionally in combination with any or all the various embodiments disclosed herein, the filter stack comprises a first filter, a second filter, and a third filter, where— the first filter having multiple holes of a size that is the same ranging from about 2.2 mm to about 1.45 mm;

the second filter having multiple holes of alternating sizes where one size that is the same ranging from about 1.8 mm to 0.9 mm and another size that is the same ranging from about 1.35 mm to about 0.6 mm; and the third filter having multi holes of a size that is the same ranging from about 1.35 mm to about 0.45 mm.

In some embodiments of the invention method, optionally in combination with any or all the various embodiments disclosed herein, the upper housing and lower housing are joined by a tongue and groove joint joined by ultrasonic welding.

In some embodiments of the invention method, optionally in combination with any or all the various embodiments disclosed herein, the filter stack comprises more than one filters, and the more than one filters are connected via rods or tubes.

In some embodiments of the invention method, optionally in combination with any or all the various embodiments disclosed herein, the inlet and outlet comprise a Luer lock thread.

In some embodiments of the invention method, optionally in combination with any or all the various embodiments disclosed herein, the at least one of the upper housing, lower housing, the filter stack or the spiral flow effectuater is made from polycarbonate or stainless steel.

In some embodiments of the invention method, optionally in combination with any or all the various embodiments disclosed herein, the device is a disposable device.

In a further aspect of the present invention, it is provided a graft, comprising a volume of the stromal vascular fraction ("SVF") generated by a method of invention, the method comprising subjecting a volume of adipose tissue to fragmentation and separation by a device to generate a volume of fragmented adipose tissue; and subject the fragmented adipose tissue to centrifuging to generate a volume of the SVF, wherein the device is a device for adipose tissue processing, microfragmentation and facilitation of mechanical separation of adipose derived stem cells ("ADSCs"), the device comprising: an upper housing with an inlet, a lower housing with an outlet, a filter stack, and a spiral flow effectuate, where— the upper housing and the lower housing are configured to join to form an enclosure that encloses the filter stack and the spiral flow effectuater; and the spiral effectuate is configured to receive a flower of filtrate from the filter stack and generate a spiral flow of the adipose tissue to minimize a direct shock of the adipose tissue with walls of the filter stacker to promote enhanced mechanical separation with less trauma to cells of the adipose tissue.

In some embodiments of the invention graft, optionally in combination with any or all the various embodiments disclosed herein, the filter stack comprises at least one filter having multiple holes of a size that is the same or different, the size ranging from about 0.4 mm to about 3 mm.

In some embodiments of the invention graft, optionally in combination with any or all the various embodiments disclosed herein, the filter stack comprises at least one filter having multiple holes of alternating sizes.

In some embodiments of the invention graft, optionally in combination with any or all the various embodiments disclosed herein, the filter stack comprises a first filter, a second filter, and a third filter, where— the first filter having multiple holes of a size that is the same ranging from about 2.2 mm to about 1.45 mm;

the second filter having multiple holes of alternating sizes where one size that is the same ranging from about 1.8 mm to 0.9 mm and another size that is the same ranging from about 1.35 mm to about 0.6 mm; and the third filter having multi holes of a size that is the same ranging from about 1.35 mm to about 0.45 mm.

In some embodiments of the invention graft, optionally in combination with any or all the various embodiments disclosed herein, the upper housing and lower housing are joined by a tongue and groove joint joined by ultrasonic welding.

In some embodiments of the invention graft, optionally in combination with any or all the various embodiments disclosed herein, the filter stack comprises more than one filters, and the more than one filters are connected via rods or tubes.

In some embodiments of the invention graft, optionally in combination with any or all the various embodiments disclosed herein, the inlet and outlet comprise a Luer lock thread.

In some embodiments of the invention graft, optionally in combination with any or all the various embodiments disclosed herein, the at least one of the upper housing, lower housing, the filter stack or the spiral flow effectuater is made from polycarbonate or stainless steel.

In some embodiments of the invention graft, optionally in combination with any or all the various embodiments disclosed herein, the device is a disposable device.

In some embodiments of the invention graft, optionally in combination with any or all the various embodiments disclosed herein, the graft further comprises a pharmaceutically acceptable carrier.

In some embodiments of the invention graft, optionally in combination with any or all the various embodiments disclosed herein, the graft further comprises a volume of adipose tissue.

In a further aspect of the present invention, it is provided a method of treating a condition in a subject, comprising administering a site of the subject in need thereof a graft of invention, the graft comprising a volume of the stromal vascular fraction ("SVF") generated by a method of invention, the method comprising subjecting a volume of adipose tissue to fragmentation and separation by a device to generate a volume of fragmented adipose tissue; and subject the fragmented adipose tissue to centrifuging to generate a volume of the SVF, wherein the device is a device for adipose tissue processing, microfragmentation and facilitation of mechanical separation of adipose derived stem cells ("ADSCs"), the device comprising: an upper housing with an inlet, a lower housing with an outlet, a filter stack, and a spiral flow effectuate, where— the upper housing and the lower housing are configured to join to form an enclosure that encloses the filter stack and the spiral flow effectuater; and the spiral effectuate is configured to receive a flower of filtrate from the filter stack and generate a spiral flow of the adipose tissue to minimize a direct shock of the adipose tissue with walls of the filter stacker to promote enhanced mechanical separation with less trauma to cells of the adipose tissue.

In some embodiments of the invention method, optionally in combination with any or all the various embodiments disclosed herein, the filter stack comprises at least one filter having multiple holes of a size that is the same or different, the size ranging from about 0.4 mm to about 3 mm.

In some embodiments of the invention method, optionally in combination with any or all the various embodiments disclosed herein, the filter stack comprises at least one filter having multiple holes of alternating sizes.

In some embodiments of the invention method, optionally in combination with any or all the various embodiments disclosed herein, the filter stack comprises a first filter, a second filter, and a third filter, where— the first filter having multiple holes of a size that is the same ranging from about 2.2 mm to about 1.45 mm;

the second filter having multiple holes of alternating sizes where one size that is the same ranging from about 1.8 mm to 0.9 mm and another size that is the same ranging from about 1.35 mm to about 0.6 mm; and the third filter having multi holes of a size that is the same ranging from about 1.35 mm to about 0.45 mm.

In some embodiments of the invention method, optionally in combination with any or all the various embodiments disclosed herein, the upper housing and lower housing are joined by a tongue and groove joint joined by ultrasonic welding.

In some embodiments of the invention method, optionally in combination with any or all the various embodiments disclosed herein, the filter stack comprises more than one filters, and the more than one filters are connected via rods or tubes.

In some embodiments of the invention method, optionally in combination with any or all the various embodiments disclosed herein, the inlet and outlet comprise a Luer lock thread.

In some embodiments of the invention method, optionally in combination with any or all the various embodiments disclosed herein, the at least one of the upper housing, lower housing, the filter stack or the spiral flow effectuater is made from polycarbonate or stainless steel.

In some embodiments of the invention graft, optionally in combination with any or all the various embodiments disclosed herein, the device is a disposable device.

In some embodiments of the invention method, optionally in combination with any or all the various embodiments disclosed herein, the graft further comprises a pharmaceutically acceptable carrier.

In some embodiments of the invention method, optionally in combination with any or all the various embodiments disclosed herein, the graft further comprises a volume of adipose tissue.

In some embodiments of the invention method, optionally in combination with any or all the various embodiments disclosed herein, the subject is a human being.

In some embodiments of the invention method, optionally in combination with any or all the various embodiments disclosed herein, the site is a skeletal site, such as a joint or intervertebral, or a soft tissue site, such as breast, cheek or buttock or a scar or wound.

BRIEF DESCRIPTION OF THE DRAWINGS

FIG. 1A shows the structural components of a device embodiment; FIG. 1B shows the outside overall appearance of a device embodiment; FIG. 1C shows the dimension of a device embodiment; and FIG. 1D shows a cross-sectional view of a device embodiment.

FIG. 7A, side view; FIG. 1B, top view; FIG. 1C, top-side view.

DETAILED DESCRIPTION OF THE INVENTION

Definitions

As used herein, the term "enhanced mechanical separation" refers to an enhanced degree of separation of stromal vascular fraction from adipose tissue without the aid of chemical or biochemical agents such as an enzyme. The use of enzyme for cell separation is a technique to separate cells from adipose tissue called for by a need to achieve such, which itself indicates that without the using an agent, it would be much harder to separate cells from adipose tissue. In this context, the term "less trauma to cells" refers to a lesser degree of trauma to cells relative to the degree of trauma to cells caused by cell separation from adipose tissue using a technology different than the one disclosed in this application, e.g., separation with enzymatic digestion or strong mechanical agitation.

As used herein, the term "condition" refers to a medical or cosmetic condition that can be addressed by ADSCs or SVF or a graft containing any of these.

Device

In one aspect of the present invention, it is provided a device for adipose tissue processing, microfragmentation and facilitation of mechanical separation of adipose derived stem cells ("ADSCs"), comprising:

an upper housing with an inlet,
a lower housing with an outlet,
a filter stack, and
a spiral flow effectuate,
wherein the upper housing and the lower housing are configured to join to form an enclosure that encloses the filter stack and the spiral flow effectuater, wherein the spiral effectuate is configured to receive a flower of filtrate from the filter stack and generate a spiral flow of the adipose tissue to minimize a direct shock of the adipose tissue with walls of the filter stacker to promote enhanced mechanical separation with less trauma to cells of the adipose tissue.

In some embodiments of the invention device, optionally in combination with any or all the various embodiments disclosed herein, the filter stack comprises at least one filter having multiple holes of a size that is the same or different, the size ranging from about 0.4 mm to about 3 mm.

In some embodiments of the invention device, optionally in combination with any or all the various embodiments disclosed herein, the filter stack comprises at least one filter having multiple holes of alternating sizes.

In some embodiments of the invention device, optionally in combination with any or all the various embodiments disclosed herein, the filter stack comprises a first filter, a second filter, and a third filter, where— the first filter having multiple holes of a size that is the same ranging from about 2.2 mm to about 1.45 mm;

the second filter having multiple holes of alternating sizes where one size that is the same ranging from about 1.8 mm to 0.9 mm and another size that is the same ranging from about 1.35 mm to about 0.6 mm; and the third filter having multi holes of a size that is the same ranging from about 1.35 mm to about 0.45 mm.

In some embodiments of the invention device, optionally in combination with any or all the various embodiments disclosed herein, the upper housing and lower housing are joined by a tongue and groove joint joined by ultrasonic welding.

In some embodiments of the invention device, optionally in combination with any or all the various embodiments disclosed herein, the filter stack comprises more than one filters, and the more than one filters are connected via rods or tubes.

In some embodiments of the invention device, optionally in combination with any or all the various embodiments disclosed herein, the inlet and outlet comprise a Luer lock thread.

In some embodiments of the invention device, optionally in combination with any or all the various embodiments disclosed herein, the at least one of the upper housing, lower housing, the filter stack or the spiral flow effectuater is made from polycarbonate or stainless steel.

In some embodiments of the invention device, optionally in combination with any or all the various embodiments disclosed herein, the device is a disposable device.

Method of Adipose Tissue Fragmentation and Separation

In another aspect of the present invention, it is provided a method of producing stromal vascular fraction of adipose tissue, comprising subjecting a volume of adipose tissue to fragmentation and separation by a device to generate a volume of fragmented adipose tissue; and subject the fragmented adipose tissue to centrifuging to generate a volume of the stromal vascular fraction, wherein the device is a device for adipose tissue processing, microfragmentation and facilitation of mechanical separation of adipose derived stem cells ("ADSCs"), the device comprising: an upper housing with an inlet, a lower housing with an outlet, a filter stack, and a spiral flow effectuate, where— the upper housing and the lower housing are configured to join to form an enclosure that encloses the filter stack and the spiral flow effectuater; and the spiral effectuate is configured to receive a flower of filtrate from the filter stack and generate a spiral flow of the adipose tissue to minimize a direct shock of the adipose tissue with walls of the filter stacker to promote enhanced mechanical separation with less trauma to cells of the adipose tissue.

In some embodiments of the invention method, optionally in combination with any or all the various embodiments disclosed herein, the filter stack comprises at least one filter having multiple holes of a size that is the same or different, the size ranging from about 0.4 mm to about 3 mm.

In some embodiments of the invention method, optionally in combination with any or all the various embodiments disclosed herein, the filter stack comprises at least one filter having multiple holes of alternating sizes.

In some embodiments of the invention method, optionally in combination with any or all the various embodiments disclosed herein, the filter stack comprises a first filter, a second filter, and a third filter, where— the first filter having multiple holes of a size that is the same ranging from about 2.2 mm to about 1.45 mm;

the second filter having multiple holes of alternating sizes where one size that is the same ranging from about 1.8 mm to 0.9 mm and another size that is the same ranging from about 1.35 mm to about 0.6 mm; and the third filter having multi holes of a size that is the same ranging from about 1.35 mm to about 0.45 mm.

In some embodiments of the invention method, optionally in combination with any or all the various embodiments disclosed herein, the upper housing and lower housing are joined by a tongue and groove joint joined by ultrasonic welding.

In some embodiments of the invention method, optionally in combination with any or all the various embodiments disclosed herein, the filter stack comprises more than one filters, and the more than one filters are connected via rods or tubes.

In some embodiments of the invention method, optionally in combination with any or all the various embodiments disclosed herein, the inlet and outlet comprise a Luer lock thread.

In some embodiments of the invention method, optionally in combination with any or all the various embodiments disclosed herein, the at least one of the upper housing, lower housing, the filter stack or the spiral flow effectuater is made from polycarbonate or stainless steel.

In some embodiments of the invention method, optionally in combination with any or all the various embodiments disclosed herein, the device is a disposable device.

Graft

In a further aspect of the present invention, it is provided a graft, comprising a volume of the stromal vascular fraction ("SVF") generated by a method of invention, the method comprising subjecting a volume of adipose tissue to fragmentation and separation by a device to generate a volume of fragmented adipose tissue; and subject the fragmented adipose tissue to centrifuging to generate a volume of the SVF, wherein the device is a device for adipose tissue processing, microfragmentation and facilitation of mechanical separation of adipose derived stem cells ("ADSCs"), the device comprising: an upper housing with an inlet, a lower housing with an outlet, a filter stack, and a spiral flow effectuate, where— the upper housing and the lower housing are configured to join to form an enclosure that encloses the filter stack and the spiral flow effectuater; and the spiral effectuate is configured to receive a flower of filtrate from the filter stack and generate a spiral flow of the adipose tissue to minimize a direct shock of the adipose tissue with walls of the filter stacker to promote enhanced mechanical separation with less trauma to cells of the adipose tissue.

In some embodiments of the invention graft, optionally in combination with any or all the various embodiments disclosed herein, the filter stack comprises at least one filter having multiple holes of a size that is the same or different, the size ranging from about 0.4 mm to about 3 mm.

In some embodiments of the invention graft, optionally in combination with any or all the various embodiments disclosed herein, the filter stack comprises at least one filter having multiple holes of alternating sizes.

In some embodiments of the invention graft, optionally in combination with any or all the various embodiments disclosed herein, the filter stack comprises a first filter, a second filter, and a third filter, where— the first filter having multiple holes of a size that is the same ranging from about 2.2 mm to about 1.45 mm;

the second filter having multiple holes of alternating sizes where one size that is the same ranging from about 1.8 mm to 0.9 mm and another size that is the same ranging from about 1.35 mm to about 0.6 mm; and the third filter having multi holes of a size that is the same ranging from about 1.35 mm to about 0.45 mm.

In some embodiments of the invention graft, optionally in combination with any or all the various embodiments disclosed herein, the upper housing and lower housing are joined by a tongue and groove joint joined by ultrasonic welding.

In some embodiments of the invention graft, optionally in combination with any or all the various embodiments disclosed herein, the filter stack comprises more than one filters, and the more than one filters are connected via rods or tubes.

In some embodiments of the invention graft, optionally in combination with any or all the various embodiments disclosed herein, the inlet and outlet comprise a Luer lock thread.

In some embodiments of the invention graft, optionally in combination with any or all the various embodiments disclosed herein, the at least one of the upper housing, lower housing, the filter stack or the spiral flow effectuater is made from polycarbonate or stainless steel.

In some embodiments of the invention graft, optionally in combination with any or all the various embodiments disclosed herein, the device is a disposable device.

In some embodiments of the invention graft, optionally in combination with any or all the various embodiments disclosed herein, the graft further comprises a pharmaceutically acceptable carrier.

In some embodiments of the invention graft, optionally in combination with any or all the various embodiments disclosed herein, the graft further comprises a volume of adipose tissue.

Method of Use of Graft

In a further aspect of the present invention, it is provided a method of treating a condition in a subject, comprising administering a site of the subject in need thereof a graft of invention, the graft comprising a volume of the stromal vascular fraction ("SVF") generated by a method of invention, the method comprising subjecting a volume of adipose tissue to fragmentation and separation by a device to generate a volume of fragmented adipose tissue; and subject the fragmented adipose tissue to centrifuging to generate a volume of the SVF, wherein the device is a device for adipose tissue processing, microfragmentation and facilitation of mechanical separation of adipose derived stem cells ("ADSCs"), the device comprising: an upper housing with an inlet, a lower housing with an outlet, a filter stack, and a spiral flow effectuate, where— the upper housing and the lower housing are configured to join to form an enclosure that encloses the filter stack and the spiral flow effectuater; and the spiral effectuate is configured to receive a flower of filtrate from the filter stack and generate a spiral flow of the adipose tissue to minimize a direct shock of the adipose tissue with walls of the filter stacker to promote enhanced mechanical separation with less trauma to cells of the adipose tissue.

In some embodiments of the invention method, optionally in combination with any or all the various embodiments disclosed herein, the filter stack comprises at least one filter having multiple holes of a size that is the same or different, the size ranging from about 0.4 mm to about 3 mm.

In some embodiments of the invention method, optionally in combination with any or all the various embodiments disclosed herein, the filter stack comprises at least one filter having multiple holes of alternating sizes.

In some embodiments of the invention method, optionally in combination with any or all the various embodiments disclosed herein, the filter stack comprises a first filter, a second filter, and a third filter, where— the first filter having multiple holes of a size that is the same ranging from about 2.2 mm to about 1.45 mm;

the second filter having multiple holes of alternating sizes where one size that is the same ranging from about 1.8 mm to 0.9 mm and another size that is the same ranging from about 1.35 mm to about 0.6 mm; and the third filter having multi holes of a size that is the same ranging from about 1.35 mm to about 0.45 mm.

In some embodiments of the invention method, optionally in combination with any or all the various embodiments disclosed herein, the upper housing and lower housing are joined by a tongue and groove joint joined by ultrasonic welding.

In some embodiments of the invention method, optionally in combination with any or all the various embodiments disclosed herein, the filter stack comprises more than one filters, and the more than one filters are connected via rods or tubes.

In some embodiments of the invention method, optionally in combination with any or all the various embodiments disclosed herein, the inlet and outlet comprise a Luer lock thread.

In some embodiments of the invention method, optionally in combination with any or all the various embodiments disclosed herein, the at least one of the upper housing, lower housing, the filter stack or the spiral flow effectuater is made from polycarbonate or stainless steel.

In some embodiments of the invention graft, optionally in combination with any or all the various embodiments disclosed herein, the device is a disposable device.

In some embodiments of the invention method, optionally in combination with any or all the various embodiments disclosed herein, the graft further comprises a pharmaceutically acceptable carrier.

In some embodiments of the invention method, optionally in combination with any or all the various embodiments disclosed herein, the graft further comprises a volume of adipose tissue.

In some embodiments of the invention method, optionally in combination with any or all the various embodiments disclosed herein, the subject is a human being.

In some embodiments of the invention method, optionally in combination with any or all the various embodiments disclosed herein, the site is a skeletal site, such as a joint or intervertebral, or a soft tissue site, such as breast, cheek or buttock or a scar or wound.

An exemplary procedure of using the SPING device is described below:

Harvest fat from any designated donor area.

Centrifuge fat from 2.5 to 3.5 min at 3000 rpm until one obtains about 20 ml of centrifuged fat.

Use the SPING 30 devices (see Example 2, below) bi-directional times (passes) to mechanically separate the ADRCs. The shorter part is the entry point and the longest the exit (see FIG. 1).

Centrifuge the fragmented fat from 4-5 min at 3000 rpm and collect the SVF that will be available on the bottom of the syringe or tube.

The SVF can be used to be directly injected on scars, wounds or joints. The SVF can be mixed with fat for autologous injection.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

The following examples illustrate rather than limit the embodiments of the present invention.

EXAMPLES

Example 1. Construction of a Device and Method for Adipose Tissue Harvesting, Microfragmentation, Facilitation of Stem Cell Extraction and Stem Cell Mechanical Separation and Nanofragmentation ("SPING")

Figure 1:
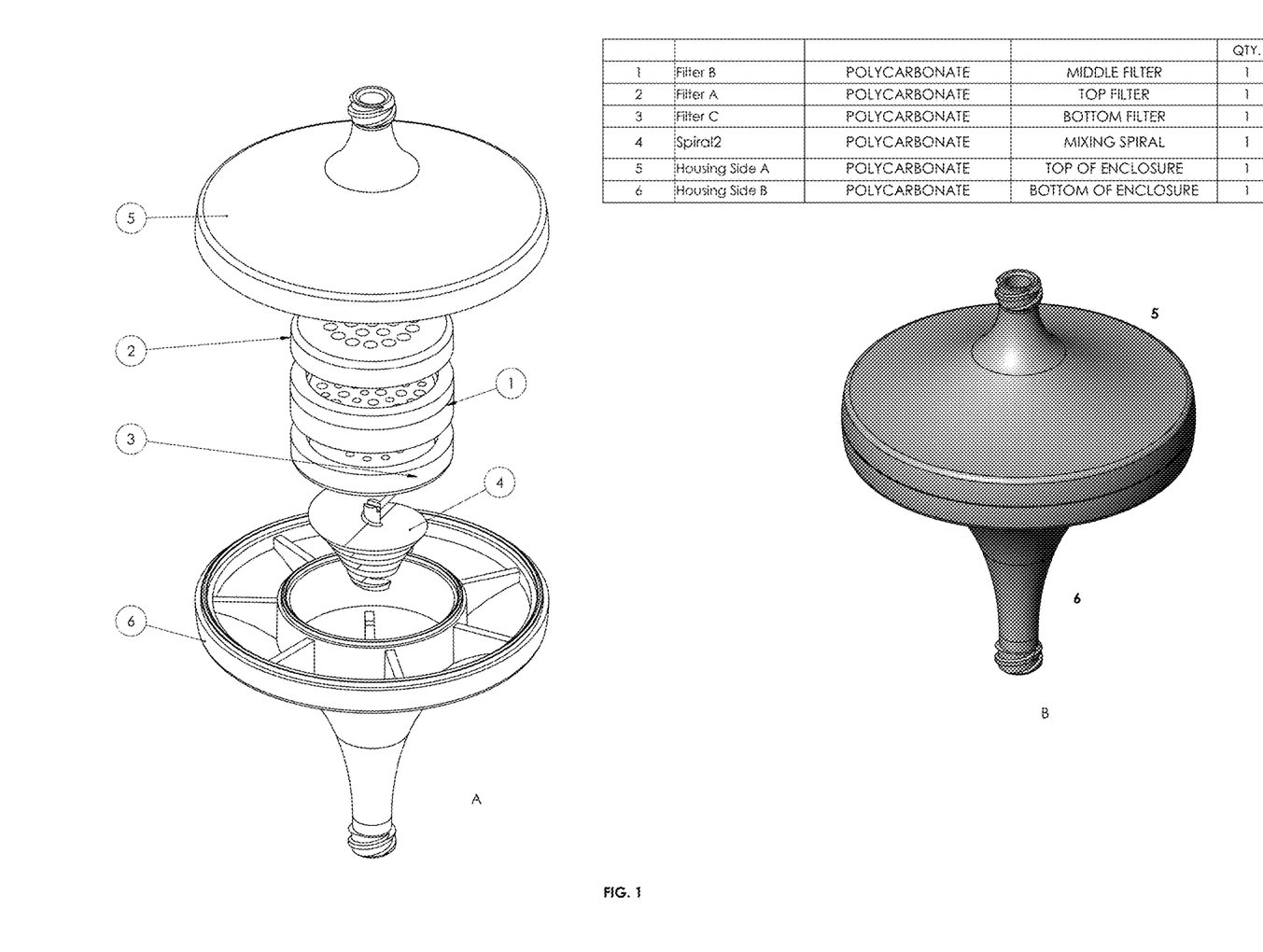
FIG. 1 shows an embodiment of the invention device.

A SPING device was constructed using polycarbonate material, and another was constructed using stainless steel. FIGS. 1-7 show the SPING device made from polycarbonate. Referring to FIG. 1, FIG. 1A shows the structural components of the SPING device, having a filter stack having Filter 1, Filter 2, Filter 3, a spiral 4, an upper housing 5, and a lower housing 6; FIG. 1B shows the outside overall appearance of the SPING device; FIG. C shows the dimension of the SPING device; and FIG. 1D shows a cross-sectional view of the SPING device.

Figure 2:
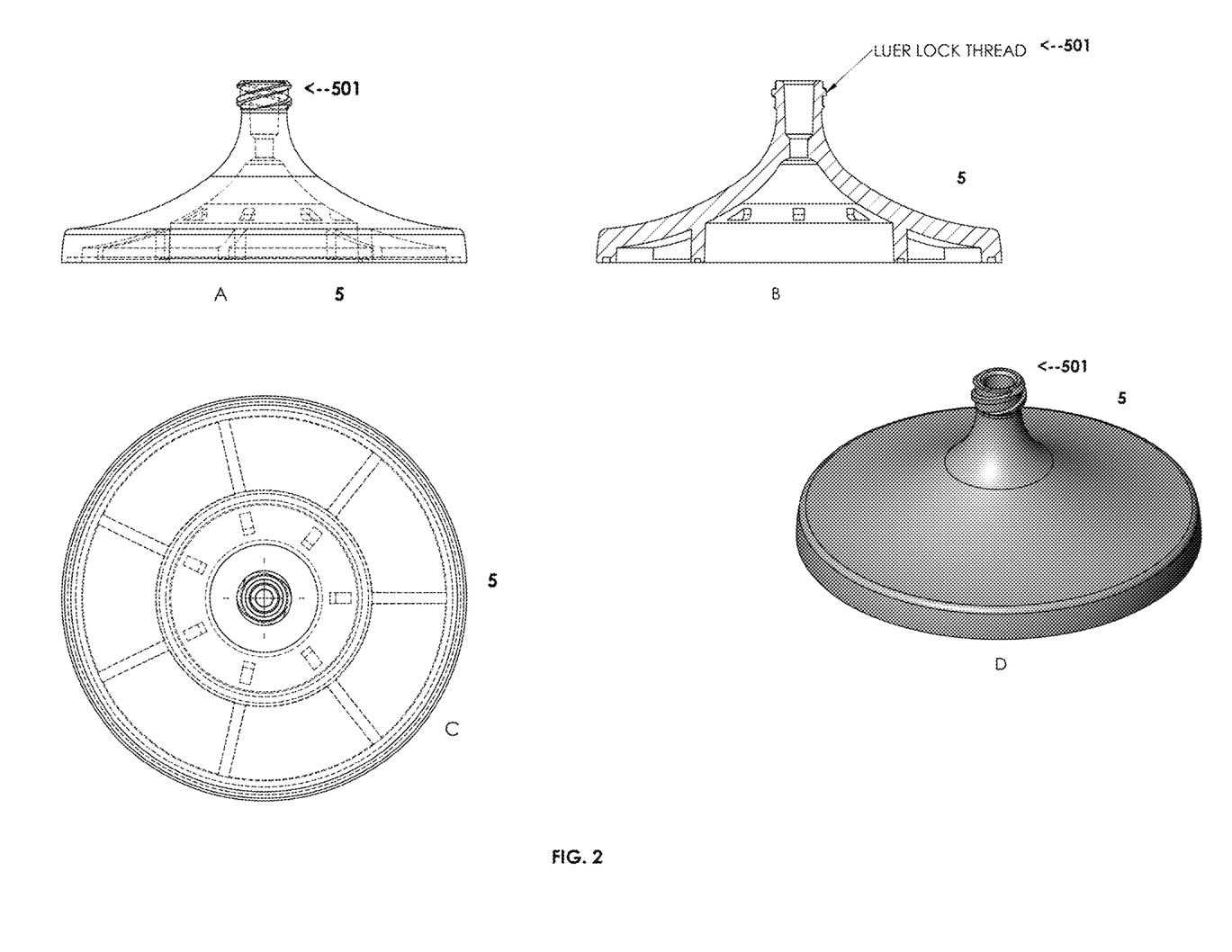
FIG. 2 shows various views of an upper housing of an embodiment of the invention device.

FIG. 2 shows various views of an upper housing 5 of the SPING device: FIG. 2A, a perspective, side view; FIG. 2B, cross-sectional view; FIG. 2C, bottom view, which faces and joins a lower housing 6 (FIG. 3); and FIG. 2D, overall appearance. 501 in FIGS. 2A, B and D is a Luer Lock thread.

Figure 3:
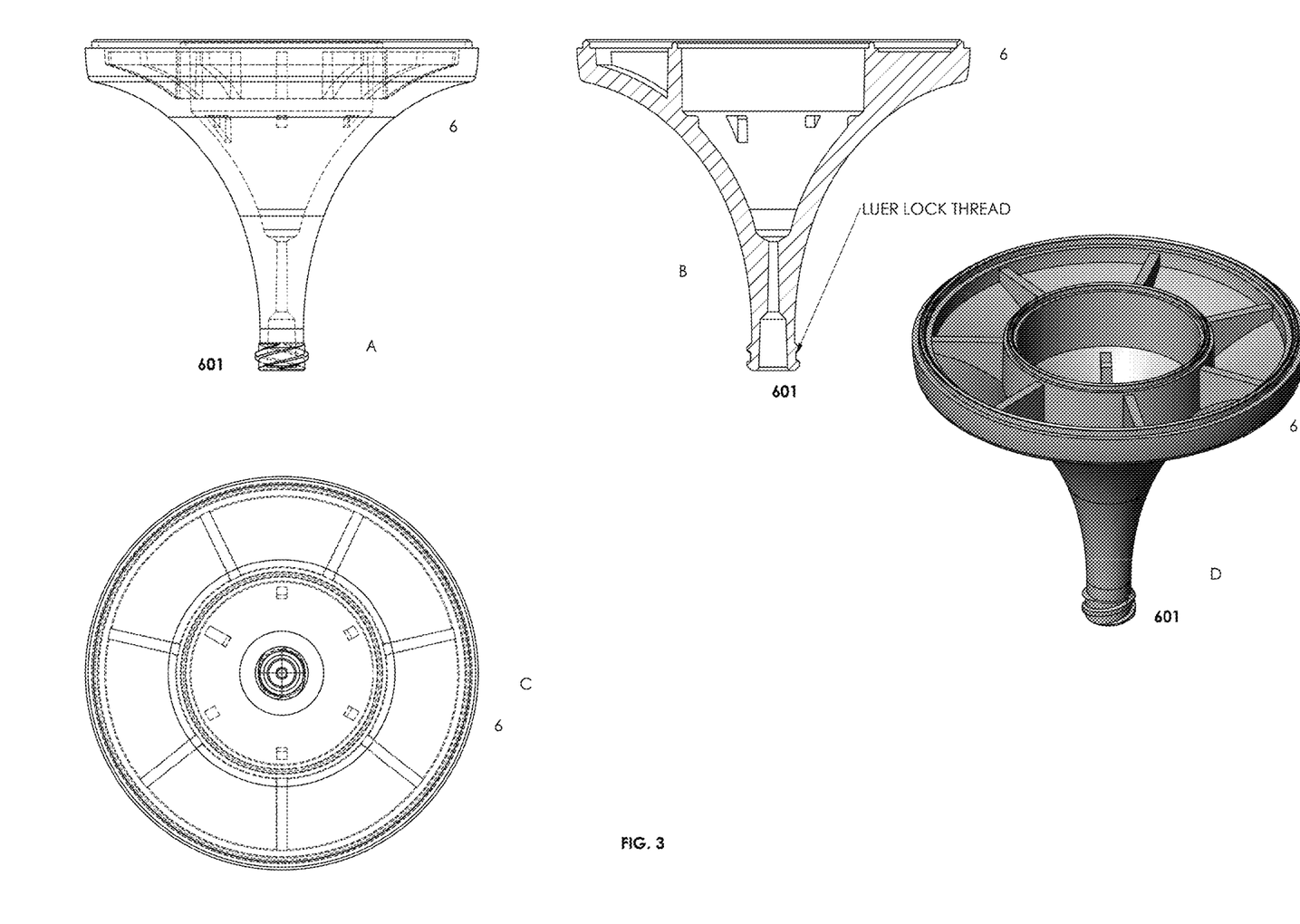
FIG. 3 shows various views of an upper housing of an embodiment of the invention device.

FIG. 3 shows various views of an upper housing of the SPING device: FIG. 3A, a perspective, side view; FIG. 3B, cross-sectional view; FIG. 3C, top view, which faces and joins an upper housing 5 (FIG. 2); and FIG. 3D, overall appearance, showing the internal housing space of the lower housing 5. 601 in FIGS. 3A, B and D is a Luer Lock thread.

Figure 4:
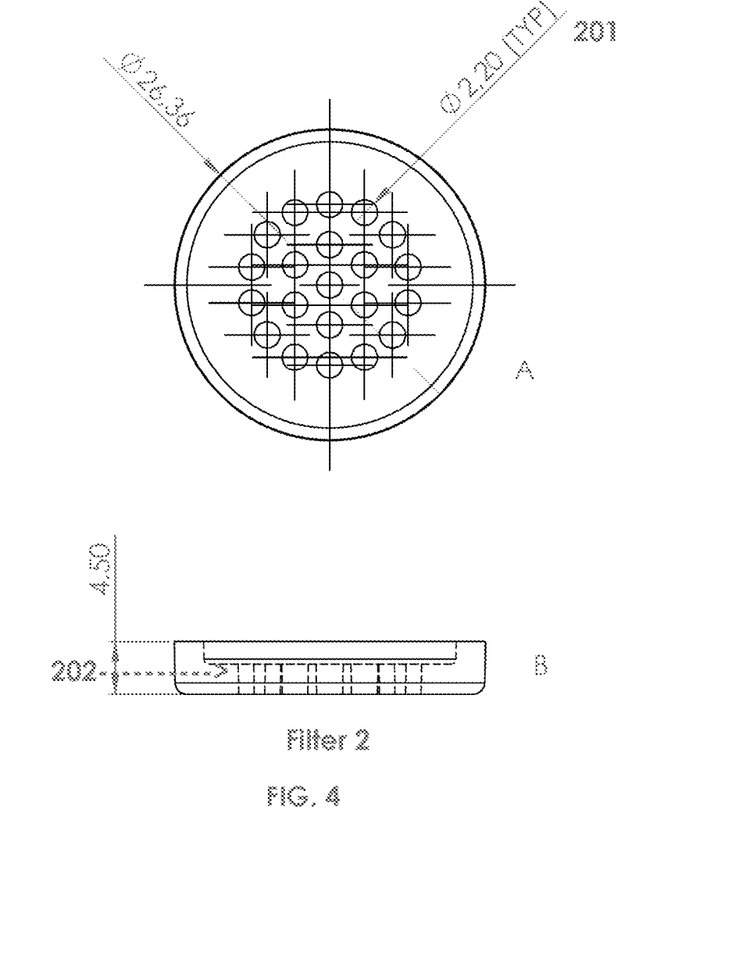
FIG. 4 shows a top view and side perspective views of filter 2 of an embodiment of invention device.

FIG. 4 shows a top view and side perspective views of Filter 2 of the SPING device: FIG. 4A, top view, showing pores of a diameter in mm 201; FIG. 4B, side view, showing pore channels 202.

Figure 5:
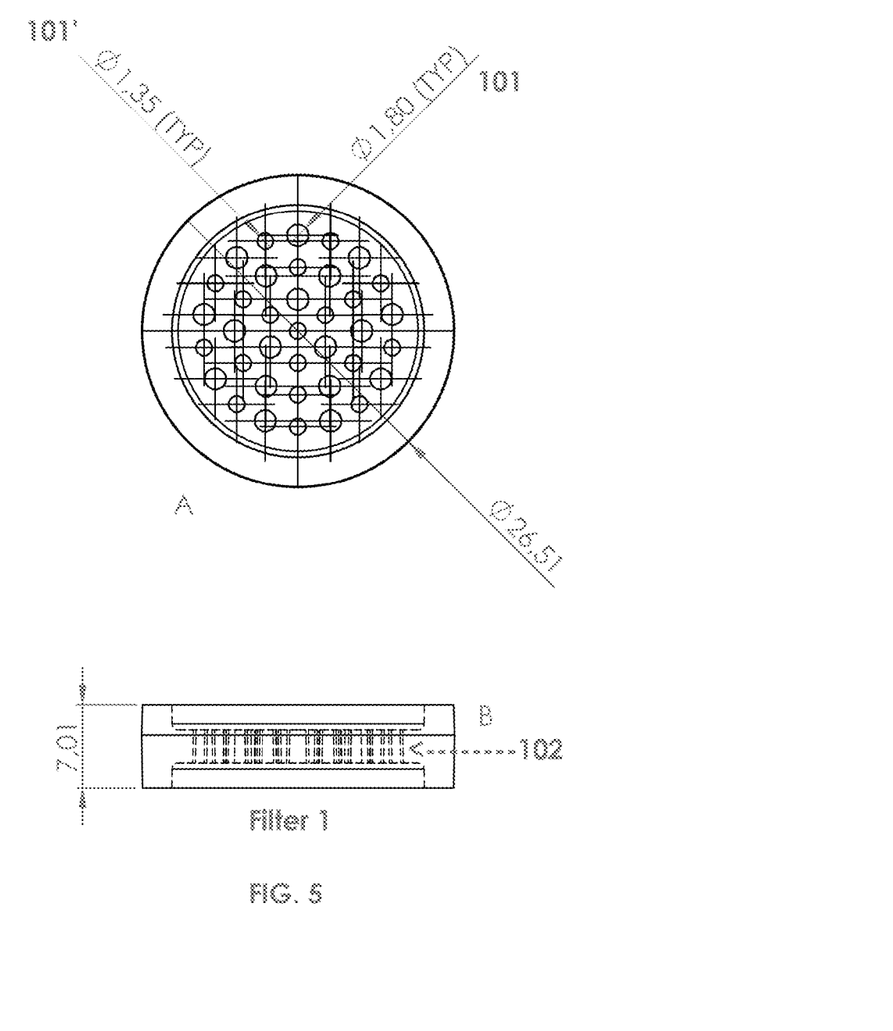
FIG. 5 shows a top view and side perspective views of filter 1 of a filter stack of an embodiment of invention device.

FIG. 5 shows a top view and side perspective views of Filter 1 of a filter stack of the SPING device: FIG. 5A, top view, showing pores 101 of two different diameters in mm (larger diameter) and 101' (smaller diameter); FIG. 5B, side view, showing pore channels 102.

Figure 6:
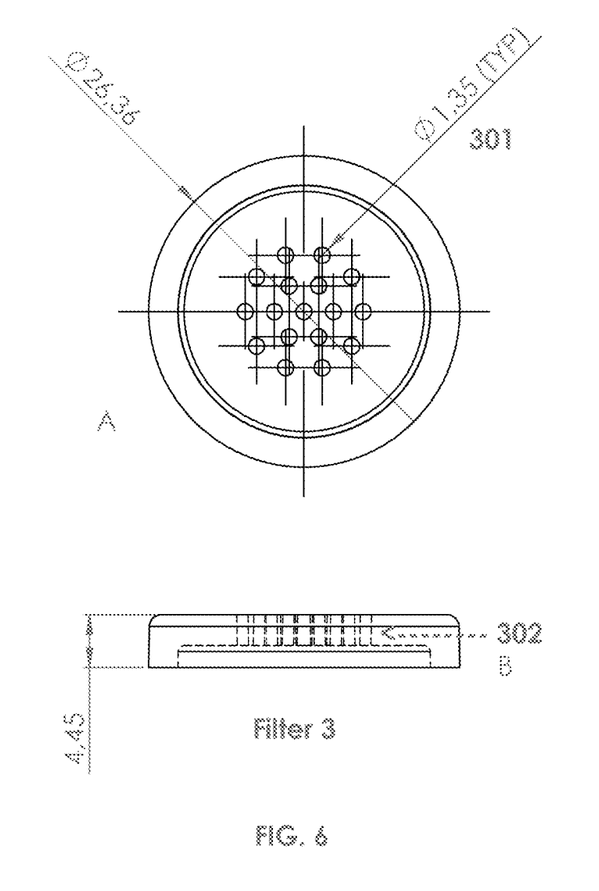
FIG. 6 shows a top view and side perspective views of filter 3 of a filter stack of an embodiment of invention device.

FIG. 6 shows a top view and side perspective views of Filter 3 of a filter stack of the SPING device: FIG. 6A, top view, showing pores 301 of a diameter in mm; FIG. 6B, side view, showing pore channels 302.

Figure 7:
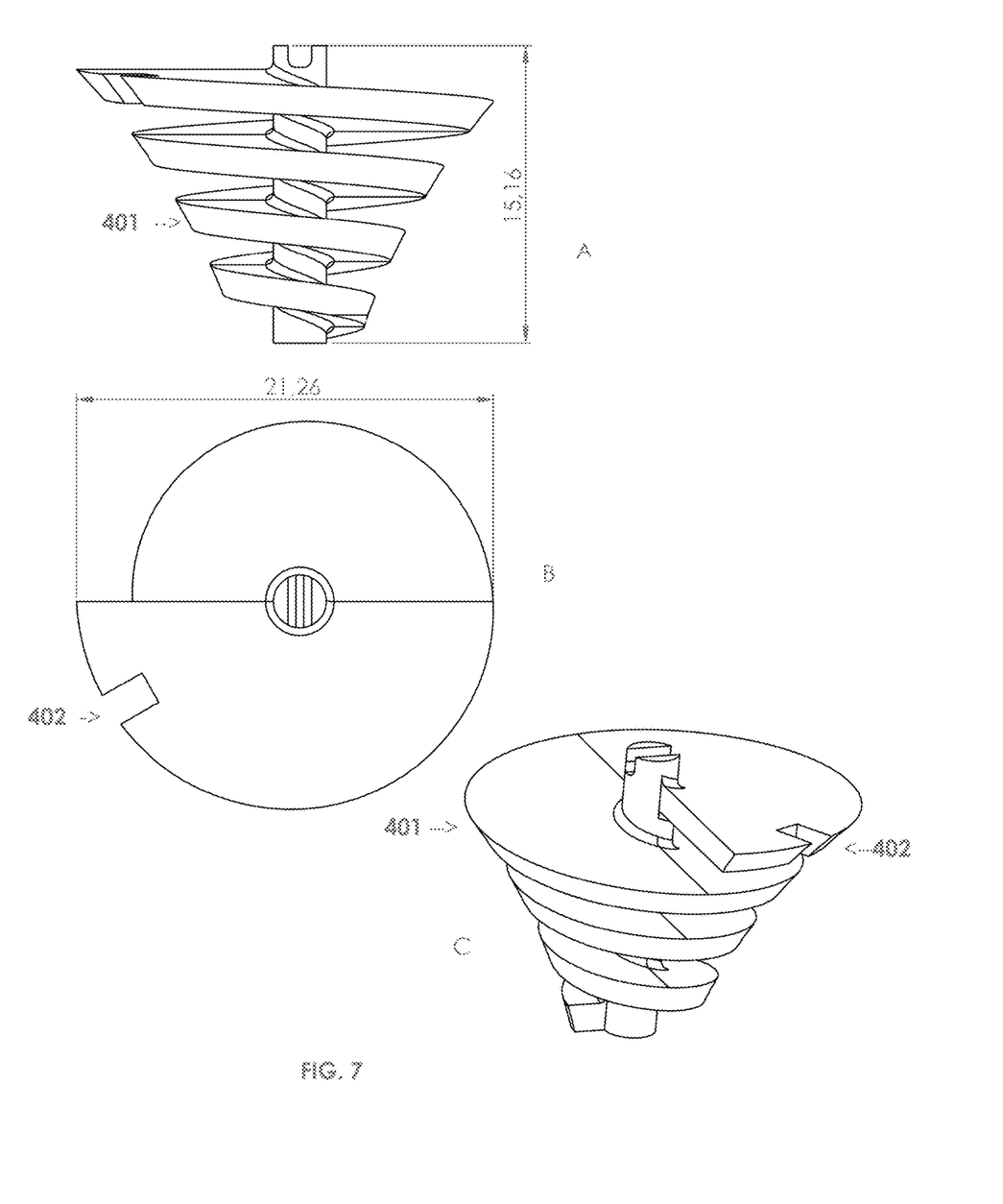
FIG. 7 shows various views of a spiral of an embodiment of invention device.

FIG. 7 shows various views of a spiral of an embodiment of invention device: FIG. 7A, side view; FIG. 7B, top view; FIG. 7C, top-side view; where 401 is the spiral component, 402 is opening for filtrate fluid.

Data for the SPING device made from stainless steel is not shown. The stainless steel SPING device and the polycarbonate SPING device were both used in the experiments of Example 2, below.

Example 2. Studies on Cell Separation Using SPING Devices: A Comparison Study

Materials and Methods

SPING devices constructed in Example 1 were used for cell separation and cell viability studies. Cell separation and cell viability studies were also performed on a device by TONNARD Technique ("Tonnard Technique device"). Adipose tissue was harvested from 5 female at the abdomen, which was stored at 4° C. for 24 hrs before use.

SPRING prototype plastic: mechanical dissociation 20 passes (MS 20);

SPRING prototype stainless steel: mechanical dissociation 30 passes (MS 30);

Tonnard Technique device: Luer to Luer, 30 passes.

TABLE 1

| Sample | Notation | Resuspension vol. (mL) | Total nucleated cells | Dilution | SVF cells per gram adipose tissue | Mean SVF cell yield |
|---|---|---|---|---|---|---|
| SPING plastic 20-1 | MS20-1 | 1 | 2.24E+06 | 5 | 1.12E+05 | 1.09E+05 |
| SPING plastic 20-2 | MS20-2 | 1 | 2.12E+06 | 5 | 1.06E+05 | |
| SPING Metal 30-1 | MS30-1 | 1 | 2.69E+06 | 5 | 1.34E+05 | 1.37E+05 |
| SPING Metal 30-2 | MS30-2 | 1 | 2.80E+06 | 5 | 1.40E+05 | |
| Tonnard-1 | ML10-1 | 1 | 6.72E+05 | 2 | 6.72E+04 | 6.97E+04 |
| Tonnard-2 | ML10-2 | 1 | 7.22E+05 | 2 | 7.22E+04 | |

Table 1 shows the SPING device (metal: stainless steel) provides the best cell separation result and SVF yield. Compared to Tonnard devices, SPING devices produced SVF cells almost twice as many, which is significant.

Figure 8:
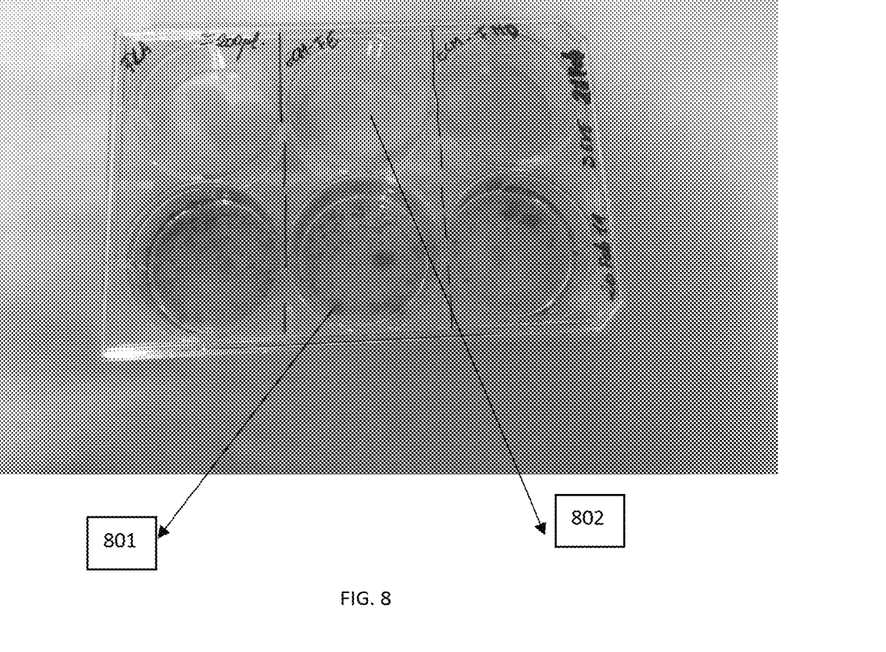
FIG. 8 shows the photo pictures of test results of cells separated by an embodiment of invention device and cells by a commercially available device.

Cell culture studies were performed on SVF cells obtained by SPING devices in comparison with that on SVF cells obtained by Tonnard devices. After 14 days culture, SVF cells by the SPING device were shown to be alive, while cells by Tonnard devices were shown to be dead (FIG. 8: SPING SVF cells 801, bottom, shown alive via dye, purple; Tonnard SVF cells 802, top, shown dead via dye, no color).

The results shown in Example 2 are even more convincing and demonstrate that SPING devices generate SVF cells almost twice as efficient as compared with the Tonnard devices. The culture cell viability studies clearly demonstrate that due to reduced impact on cells by SPING device and that the SVF are convincingly far more viable as compared with SVF cells obtained by Tonnard devices, which is very significant in cell regeneration and cell therapy.

Those skilled in the art will know, or be able to ascertain, using no more than routine experimentation, many equivalents to the specific embodiments of the invention described herein. These and all other equivalents are intended to be encompassed by the following claims.

I claim:

1. A device for adipose tissue processing, microfragmentation and facilitation of mechanical separation of adipose derived stem cells ("ADSCs"), comprising:
   an upper housing with an inlet,
   a lower housing with an outlet,
   a filter stack, and
   a spiral flow effectuater,
   wherein the upper housing and the lower housing are configured to join to form an enclosure that encloses the filter stack and the spiral flow effectuater,
   wherein the spiral effectuater comprises spiral ridges and grooves and is configured to immediately attach to the filter stack and receive a flower of filtrate from the filter stack and generate a spiral flow of the adipose tissue, whereby minimizing a direct shock of the adipose tissue with walls of the filter stacker so as to promote enhanced mechanical separation with less trauma to cells of the adipose tissue, and
   wherein the spiral effectuater is configured to be locked in a fixed position with respect to the upper housing, the lower housing, and the filter stack.

2. The device according to claim 1, wherein the filter stack comprises at least one filter having multiple holes of a size that is the same or different, the size ranging from about 0.4 mm to about 3 mm.

3. The device according to claim 1, wherein the filter stack comprises at least one filter having multiple holes of alternating sizes.

4. The device according to claim 1, wherein the filter stack comprises a first filter, a second filter, and a third filter, where—
   the first filter having multiple holes of a size that is about 2.2 mm;
   the second filter having multiple holes of alternating sizes where one size that is about 1.8 mm and another size that is 1.35 mm; and
   the third filter having multi holes of a size that is about 1.35 mm.

5. The device according to claim 1, wherein the upper housing and lower housing are joined by a tongue and groove joint joined by ultrasonic welding.

6. The device according to claim 1, wherein the filter stack comprises more than one filters, and the more than one filters are connected via rods or tubes.

7. The device according to claim 1, wherein the inlet and outlet comprise a Luer lock thread.

8. The device according to claim 1, wherein at least one of the upper housing, lower housing, the filter stack or the spiral flow effectuater is made from polycarbonate or stainless steel.

9. The device according to claim 1, which is a disposable device.

10. A method of producing stromal vascular fraction of adipose tissue, comprising:
    providing the device according to claim 1,
    subjecting a volume of adipose tissue to fragmentation and separation by the device to generate a volume of fragmented adipose tissue, and
    subject the fragmented adipose tissue to centrifuging to generate a volume of the stromal vascular fraction.

11. The method according to claim 10, wherein the filter stack comprises at least one filter having multiple holes of a size that is the same or different, the size ranging from about 0.4 mm to about 3 mm.

12. The method according to claim 10, wherein the filter stack comprises at least one filter having multiple holes of alternating sizes.

13. The method according to claim 10, wherein the filter stack comprises a first filter, a second filter, and a third filter, where— the first filter having multiple holes of a size that is about 2.2 mm;
the second filter having multiple holes of alternating sizes where one size that is about 1.8 mm and another size that is about 1.35 mm; and
the third filter having multi holes of a size that is the same ranging from about 1.35 mm to about 0.45 mm.

14. A graft, comprising a volume of the stromal vascular fraction ("SVF") generated according to claim 10.

15. The graft according to claim 11, further comprising a pharmaceutically acceptable carrier.

16. The graft according to claim 11, further comprising a volume of adipose tissue.

\* \* \* \* \*